United States Patent [19]

Tsuboniwa et al.

[11] Patent Number: 5,532,360
[45] Date of Patent: Jul. 2, 1996

[54] METHOD FOR HANDLING (2-ALKYL)ACRYLOYL ISOCYANATE, METHOD FOR STABILIZING (2-ALKYL)ACRYLOYL ISOCYANATE, METHOD FOR PRODUCING (2-ALKYL)ACRYLOYL ISOCYANATE, HETEROCYCLIC COMPOUND, AND METHOD FOR PRODUCING HETEROCYCLIC COMPOUND

[75] Inventors: Noriyuki Tsuboniwa, Osaka; Satoshi Urano, Kyoto; Otohiko Tsuge, Fukuoka; Taizo Hatta, Kumamoto, all of Japan

[73] Assignee: Nippon Paint Co., Ltd., Osaka, Japan

[21] Appl. No.: 400,588

[22] Filed: Mar. 8, 1995

[30] Foreign Application Priority Data

Mar. 11, 1994 [JP] Japan .................................. 6-067867

[51] Int. Cl.⁶ ................................................ C07D 273/04
[52] U.S. Cl. ................................................ 544/68; 562/871
[58] Field of Search ................................. 562/871; 544/68

[56] References Cited

U.S. PATENT DOCUMENTS 3,979,421 9/1976 Zecher et al. .

FOREIGN PATENT DOCUMENTS 0143613 6/1985 European Pat. Off. .
0177122 4/1986 European Pat. Off. .

Primary Examiner—José G. Dees
Assistant Examiner—Joseph M. Conrad, III
Attorney, Agent, or Firm—Sughrue, Mion, Zinn, Macpeak & Seas

[57] ABSTRACT

A method for handling and stabilizing a (2-alkyl)-acryloyl isocyanate represented by the formula (1)

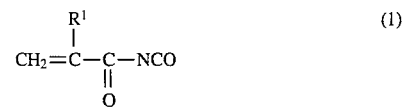

is disclosed, which comprises the steps of:

reacting an azomethine compound represented by formula (2)

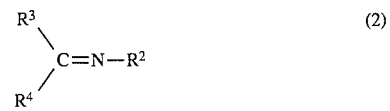

with the (2-alkyl)-acryloyl isocyanate of formula (1) to obtain the reaction product of formula (3)

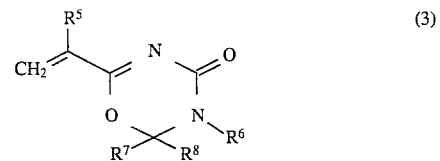

and dissolving said reaction product into a solvent to regenerate the (2-alkyl)-acryloyl isocyanate of formula (1); the identity of said solvent and R-groups being defined herein.

10 Claims, No Drawings

METHOD FOR HANDLING (2-ALKYL)ACRYLOYL ISOCYANATE, METHOD FOR STABILIZING (2-ALKYL)ACRYLOYL ISOCYANATE, METHOD FOR PRODUCING (2-ALKYL)ACRYLOYL ISOCYANATE, HETEROCYCLIC COMPOUND, AND METHOD FOR PRODUCING HETEROCYCLIC COMPOUND

FIELD OF THE INVENTION

The present invention relates to a method for handling an acyl isocyanate compound, a method for stabilizing the acyl isocyanate compound, a method for producing the acyl isocyanate compound, a heterocyclic compound, and a method for producing the heterocyclic compound. Particularly, the present invention relates to a method for handling a (2-alkyl)acryloyl isocyanate, a method for stabilizing the (2-alkyl)acryloyl isocyanate, a method for producing the (2-alkyl)acryloyl isocyanate, a novel heterocyclic compound, and a method for producing the novel heterocyclic compound.

BACKGROUND OF THE INVENTION (2-Alkyl)acryloyl isocyanates represented by acryloyl isocyanate, methacryloyl isocyanate, and the like contain a polymerizable carbon-carbon unsaturated group and an isocyanate group in the same molecule. Since these functional groups react with different mechanisms to participate in various reactions, utilization of (2-alkyl)acryloyl isocyanates in the fields of synthesis chemistry, polymer chemistry, etc., is expected.

For example, European Patent Application No. 0177122-A (corresponding to JP-A-60-231644) discloses use of a (2-alkyl)acryloyl isocyanate for synthesizing a novel compound represented by formula (4):

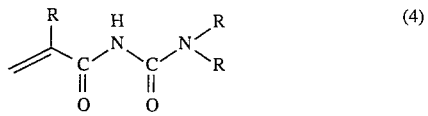

(wherein R's may be the same or different and each represents a lower alkyl group). (The term "JP-A" as used herein means an "unexamined published Japanese patent application.")

Further, European Patent Application No. 0177122-A (corresponding to JP-A-61-17554) discloses the use of a (2-alkyl)acryloyl isocyanate for synthesizing a novel compound represented by formula (5):

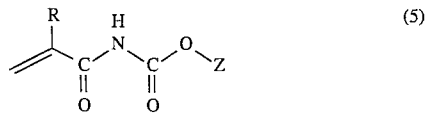

(wherein R represents a lower alkyl group and Z represents an organic group having a tertiary amino group).

Both of the novel compounds respectively represented by formulae (4) and (5) have been proved to be useful in the fields of paints and plastics. It is therefore increasingly expected that other useful novel compounds will be synthesized from (2-alkyl)acryloyl isocyanates.

Although (2-alkyl)acryloyl isocyanates, which are expected to be effectively utilized, are stable compounds which are liquid at ordinary temperature, it is difficult to handle them. Specifically, the (2-alkyl)acryloyl isocyanates are extremely reactive with moisture in air and are thus readily denatured. In addition, the isocyanates have a strong irritating odor and tend to impair working conditions. Because of these, the (2-alkyl)acryloyl isocyanates should be carefully handled using a syringe, etc.

SUMMARY OF THE INVENTION

An object of the present invention is to facilitate the handling of a (2-alkyl)acryloyl isocyanate.

Another object of the present invention is to easily stabilize the (2-alkyl)acryloyl isocyanate.

Still another object of the present invention is to produce the (2-alkyl)acryloyl isocyanate in a simplified manner.

A further object of the present invention is to provide a novel heterocyclic compound.

Still a further object of the present invention is to provide a method for producing the novel heterocyclic compound.

The handling method and stabilization method according to the present invention are methods for handling and stabilizing a (2-alkyl)acryloyl isocyanate represented by formula (1):

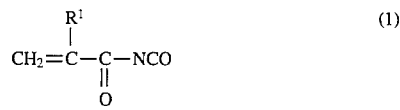

(wherein $R^1$ represents a hydrogen atom or a lower alkyl group).

This handling method may comprise the steps of reacting an azomethine compound represented by formula (2) with the (2-alkyl)acryloyl isocyanate to obtain a reaction product and dissolving crystals of this reaction product into a solvent to regenerate the (2-alkyl)acryloyl isocyanate;

(wherein $R^2$ represents an alkyl group, a cycloalkyl group, an aralkyl group, an alkenyl group, or an alkynyl group, and $R^3$ and $R^4$ each represents a hydrogen atom or a group which does not cause tautomerism with C=N in the formula, provided that at least one of $R^3$ and $R^4$ is not a hydrogen atom).

The method for handling a (2-alkyl)acryloyl isocyanate, according to the present invention, may also comprise the steps of reacting an azomethine compound represented by formula (2) with the (2-alkyl)acryloyl isocyanate to obtain a compound represented by formula (3) and dissolving this compound into a solvent to regenerate the (2-alkyl)acryloyl isocyanate;

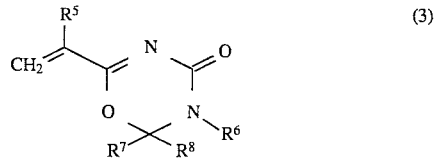

(wherein $R^5$, $R^6$, $R^7$, and $R^8$ each is the same as $R^1$, $R^2$, $R^3$, and $R^4$, respectively, defined in formulae (1) and (2)).

The method for stabilizing a (2-alkyl)acryloyl isocyanate, according to the present invention, comprises the steps of preparing an azomethine compound represented by formula (2) and reacting this azomethine compound with the (2-alkyl)acryloyl isocyanate to form a heterocyclic compound represented by formula (3).

The method of the present invention for producing a (2-alkyl)acryloyl isocyanate comprises the steps of preparing a heterocyclic compound represented by formula (3) and dissolving this heterocyclic compound into a solvent.

The novel compound of the present invention is a heterocyclic compound represented by formula (3).

The method of the present invention for producing a heterocyclic compound is a method for producing the novel heterocyclic compound represented by formula (3). This method comprises the steps of preparing a (2-alkyl)acryloyl isocyanate represented by formula (1), preparing an azomethine compound represented by formula (2), and reacting the (2-alkyl)acryloyl isocyanate with the azomethine compound.

DETAILED DESCRIPTION OF THE INVENTION

Handling Method

In the handling method of the present invention, a (2-alkyl)acryloyl isocyanate represented by formula (1) is handled.

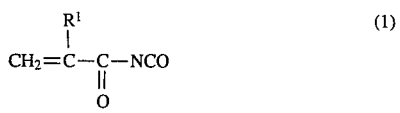
(1)

In formula (1), $R^1$ represents hydrogen or a lower alkyl group. The lower alkyl group herein means an alkyl group having 1 to 5 carbon atoms. This alkyl group may be branched. Examples of the alkyl group include methyl, ethyl, n-propyl, isopropyl, n-butyl, t-butyl, sec-butyl, and pentyl.

Especially preferred in the present invention are methacryloyl isocyanate, represented by formula (1) wherein $R^1$ is methyl, and acryloyl isocyanate, represented by formula (1) wherein $R^1$ is a hydrogen atom.

(First Step)

In this method for handling the (2-alkyl)acryloyl isocyanate, an azomethine compound represented by formula (2) is first reacted with the (2-alkyl)acryloyl isocyanate to stabilize the isocyanate.

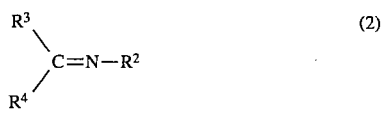
(2)

In formula (2), $R^2$ represents an alkyl group, a cycloalkyl group, an aralkyl group, an alkenyl group, or an alkynyl group.

The alkyl group preferably has 1 to 18 carbon atoms. The alkyl group may be linear or branched, and may be a primary, secondary, or tertiary alkyl group. Examples of the primary alkyl group include methyl, ethyl, propyl, butyl, isobutyl, hexyl, 3-ethylhexyl, octyl, and octadecyl. Examples of the secondary alkyl group include isopropyl, 1,5-dimethylhexyl, and 1-ethylpropyl. Examples of the tertiary alkyl group include t-butyl and t-octyl.

The cycloalkyl group preferably has not more than 18 carbon atoms (particularly 3 to 18 carbon atoms). Examples of such cycloalkyl groups include cyclohexyl, cyclopentyl, adamantyl, and cyclodecyl.

The aralkyl group preferably has not more than 18 carbon atoms (particularly 6 to 18 carbon atoms). Examples of such aralkyl groups include benzyl, phenylbenzyl, and 4-phenylbenzyl.

The alkenyl group preferably has not more than 18 carbon atoms (particularly 3 to 18 carbon atoms). This alkenyl group may be linear or branched, and may contain a cyclic structure. Examples of such alkenyl groups include allyl, oleyl, and 2-cyclohexenyl.

The alkynyl group preferably has not more than 6 carbon atoms (particularly 3 to 6 carbon atoms), and may be linear or branched. Examples of such alkynyl groups include propargyl.

The alkyl group described above may be partly substituted with a halogen or an alkoxy group. The cycloalkyl, aralkyl, alkenyl, and alkynyl groups described above each may be partly substituted with at least one of an alkyl group, halogen, nitro group, cyano group, alkoxy group, and silyl group.

In formula (2), $R^3$ and $R^4$ each represents a group which does not cause tautomerism with C=N in formula (2). Examples of such group include a hydrogen atom and a group in which a carbon atom located in the α-position to carbon atoms constituting a hetercyclic ring does not have a hydrogen atom.

Examples of the group in which the α-position carbon does not have a hydrogen atom include aryl groups, e.g., phenyl, p-methylphenyl, p-chlorophenyl, o-ethoxyphenyl, p-nitrophenyl, biphenyl, m-phenoxyphenyl, 2-naphthyl, and 9-anthranyl; heterocyclic groups, e.g., pyridyl, furyl, and 3-thienyl; alkaryl groups, e.g., tolyl and xylyl; and tertiary alkyl groups, e.g., t-butyl and 2,2-dimethylpentenyl. These groups each may be partly substituted with at least one of alkyl group, halogen, nitro group, cyano group, alkoxy group, silyl group, and phenyl group. $R^3$ and $R^4$ may be the same or different, provided that at least one of $R^3$ and $R^4$ is not a hydrogen atom.

Specific examples of the azomethine compound represented by such formula (2) include p-methylbenzylidenebenzylamine, p-methoxybenzylidenebenzylamine, p-chlorobenzylidenebenzylamine, p-phenylbenzylidenebenzylamine, naphthylmethylidenebenzylamine, furylmethylidene-n-butylamine, vinylidenecyclohexylamine, benzylidenecyclohexylamine, benzylidene-n-butylamine, benzylideneoctadecylamine, benzylidenebenzylamine, benzylideneallylamine, benzylidene-t-butylamine, α-phenyl-p-methylbenzylidenebenzylamine, α-phenylbenzylidenecyclohexylamine, α-naphthylbenzylidenebenzylamine, α-p-chlorophenylbenzylidenebenzylamine, α-t-butylbenzylidenebenzylamine, and 2,2-dimethylpropylidenebenzylamine.

In reacting the (2-alkyl)acryloyl isocyanate with the azomethine compound described above, the azomethine compound is used in an amount of preferably from 0.5 to 5 equivalents, particularly preferably from 1.0 to 1.5 equivalents, per 1 equivalent of the (2-alkyl)acryloyl isocyanate. The reaction temperature is desirably regulated in the range of from −20° to 50° C. If the reaction temperature is lower than −20° C., the reaction proceeds with difficulty, so that the stabilization treatment is required for a longer time. On the other hand, if the reaction is carried out at a temperature of higher than 50° C., there is a fear that the reaction product may be decomposed to make the attainment of the object impossible. The reaction temperature is particularly preferably at room temperature (e.g., from 10° to 25° C.).

This reaction (step) may be performed without or using a solvent.

In the case of using a solvent, the solvent is not particularly limited in kind as long as it does not adversely influence the reaction of the (2-alkyl)acryloyl isocyanate with the azomethine compound. Solvents having active hydrogen, such as, e.g., alcohols, cannot be used because such solvents are highly reactive with the (2-alkyl)acryloyl isocyanate. It is necessary that any usable solvent should be sufficiently dehydrated before use, since the (2-alkyl)acryloyl isocyanate is highly reactive with water.

Examples of solvents usable in the above reaction include aliphatic hydrocarbons, e.g., hexane and heptane; aromatic hydrocarbons, e.g., benzene and toluene; ethers, e.g., diethyl ether, dibutyl ether, and dioxane; halogenated hydrocarbons, e.g., methylene chloride, ethylene chloride, dichloroethane, dichlorobenzene, chloroform, and carbon tetrachloride; and ketones, e.g., methyl ethyl ketone, methyl isobutyl ketone, and acetone.

The reaction described above is completed earlier by precipitating the resulting heterocyclic compound as crystals (described later). The precipitation of the heterocyclic compound as crystals is accelerated by conducting the reaction using a nonpolar solvent, in particular, a nonpolar solvent having a dielectric constant of less than 5. Examples of the solvent having a dielectric constant of less than 5 include aliphatic hydrocarbons, e.g., hexane and heptane; aromatic hydrocarbons, e.g., benzene and toluene; and ethers, e.g., diethyl ether, dibutyl ether, and dioxane.

The reaction described above yields crystals. These crystals consist of a heterocyclic compound represented by formula (3).

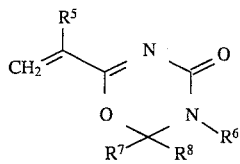

(3)

In this heterocyclic compound, $R^5$, $R^6$, $R^7$, and $R^8$ each is the same as $R^1$, $R^2$, $R^3$, and $R^4$, respectively, defined in formulae (1) and (2) described above.

The (2-alkyl)acryloyl isocyanate is stabilized by being converted into such heterocyclic compound. This heterocyclic compound can be easily isolated by filtration. In filtration, the reaction system is preferably cooled to −20° C. or lower; this cooling brings about an increased recovery.

(Second Step)

The subsequent step in the handling method of the present invention is to regenerate the (2-alkyl)acryloyl isocyanate from the heterocyclic compound. In this step, crystals of the heterocyclic compound are dissolved into a solvent in which the crystals are soluble. Usable solvents include halogenated hydrocarbons (e.g., chloroform); esters (e.g., ethyl acetate and dimethyl carbonate); ketones (e.g., methyl isobutyl ketone); and amides (e.g., N-methylpyrrolidone). Especially preferred are polar solvents having a dielectric constant of 5 or higher.

Upon dissolution of crystals of the heterocyclic compound into a solvent, the heterocyclic compound dissociates into the (2-alkyl)acryloyl isocyanate and the azomethine compound both used as starting compounds. This dissolution is desirably conducted at room temperature or at a higher temperature of 100° C. or less. If the temperature for dissolution is lower than room temperature, the heterocyclic compound is dissociated with difficulty, resulting in a decreased degree of regeneration of the (2-alkyl)acryloyl isocyanate. On the other hand, if the temperature for dissolution is too high, there is a fear that the (2-alkyl)acryloyl isocyanate regenerated through dissociation may be subjected to a side reaction. The particularly preferred dissolution temperature is from 40° to 60° C.

The (2-alkyl)acryloyl isocyanate thus-obtained by dissolving the heterocyclic compound into a solvent can be used as it is for a subsequent synthesis reaction. For example, by using a solvent containing an active hydrogen compound (e.g., an alcohol), the (2-alkyl)acryloyl isocyanate can be recovered as an adduct of the active hydrogen compound. It is also possible to isolate the (2-alkyl)acryloyl isocyanate by a separation technique (e.g., distillation), before the isocyanate is used in a synthesis reaction. Consequently, according to the handling method comprising the first and second steps described above, the (2-alkyl)acryloyl isocyanate can be handled easily as compared with the case in which the isocyanate is directly used as it is.

Stabilization Method

The first step of the handling method described above can be utilized as a method for stabilizing the (2-alkyl)acryloyl isocyanate. Namely, a (2-alkyl)acryloyl isocyanate is stabilized by being converted into a stable heterocyclic compound. This stabilization method for a (2-alkyl)acryloyl isocyanate can be easily accomplished by merely mixing the (2-alkyl)acryloyl isocyanate with the azomethine compound described above. The (2-alkyl)acryloyl isocyanate thus stabilized can be regenerated by merely dissolving the heterocyclic compound formed by the stabilization into a solvent. This method is therefore effective in storing a (2-alkyl)acryloyl isocyanate over a prolonged time period or in transporting the same.

Method for Producing (2-Alkyl)acryloyl Isocyanate

The second step of the handling method described above can be utilized as a method for producing a (2-alkyl)acryloyl isocyanate. Namely, a (2-alkyl)acryloyl isocyanate can be extremely easily produced by merely dissolving the heterocyclic compound described above into a solvent.

The heterocyclic compound for use in this production method may be the heterocyclic compound produced in the first step of the handling method described above, or may be a heterocyclic compound synthesized by another chemical method.

Heterocyclic Compound and Method for Production Thereof

The heterocyclic compound obtained in the first step of the handling method described above is a novel heterocyclic compound provided first according to the present invention. This compound is a solid having a melting point and is thermally stable. It is stable also to moisture. Furthermore, the novel heterocyclic compound has a low vapor pressure and is less irritating.

Since the heterocyclic compound has a polymerizable double bond, it is expected to be used as a material for producing a polymer for use in paints, adhesives, plastics, etc. Furthermore, since the carbon-carbon double bond contained in this heterocyclic compound is highly reactive, the heterocyclic compound is also expected to be used as an intermediate for the synthesis of fine chemical products, e.g., medicines and agricultural chemicals (i.e., pesticides).

The first step of the handling method described above can be utilized as it is as the method of the present invention for synthesizing the heterocyclic compound.

The present invention will be explained below in more detail by reference to the following Examples, but the invention should not be construed as being limited thereto.

EXAMPLE 1

The azomethine compound (1.7 g: 9.0 mmol) shown in Table 1 was added in a nitrogen stream to a solution of methacryloyl isocyanate (1.0 g: 9.0 mmol), represented by the following structural formula (6), in dry benzene (10 ml). The obtained mixture was stirred at 20° C.

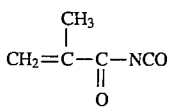

$$CH_2=C(CH_3)-C(=O)-NCO \quad (6)$$

A white precipitate was generated after 20 minutes, but stirring was further continued thereafter. After the reaction was performed over 180 minutes in total, the white precipitate yielded was separated by filtration to obtain colorless needles. The filtrate was concentrated, and the resulting solid was washed with diethyl ether to further obtain colorless needles. The yield of all these colorless needles obtained was 44%.

The crystals obtained were measured with respect to melting point, IR spectrum, and NMR spectrum. The results are shown in Table 2 below.

As is apparent from the results in Table 2, the crystals obtained were ascertained to be the novel compound represented by the following structural formula (7).

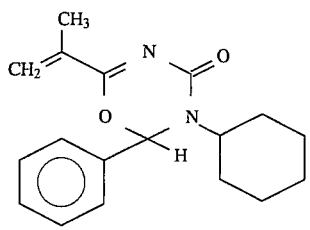

(7)

EXAMPLE 2

Using the same methacryloyl isocyanate (1.0 g: 9.0 mmol) as in Example 1, a crystal was obtained in the same manner and under the same conditions as in Example 1, except that the azomethine compound (1.96 g: 9.0 mmol) was changed to those shown in Table 1. The yield of the crystal was 54%. The crystals obtained were measured with respect to melting point, IR spectrum, and NMR spectrum. The results are shown in Table 3 below.

As is apparent from the results in Table 3, the crystals obtained were ascertained to be the novel compound represented by the following structural formula (8).

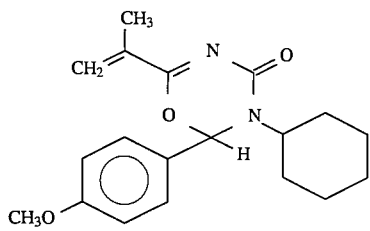

(8)

EXAMPLES 3 TO 8

The same procedure as in Example 1 was carried out, except that the azomethine compound and the reaction conditions were changed as shown in Table 1 and Table 4, respectively. Thus, crystals of heterocyclic compounds were obtained.

The structural formulae and analytical data for the heterocyclic compounds obtained are shown in Table 5 and Table 6, respectively.

TABLE 1

Azomethine compound $$\begin{array}{c} R^3 \\ \phantom{R}\diagdown \\ C=N-R^2 \\ \phantom{R}\diagup \\ R^4 \end{array}$$

| Example | $R^2$ | $R^3$ | $R^4$ |
|---|---|---|---|
| 1 | cyclohexyl | phenyl | H |
| 2 | cyclohexyl | $CH_3O$-phenyl- | H |
| 3 | phenyl-$CH_2$- | phenyl | H |
| 4 | phenyl-$CH_2$- | $CH_3$-phenyl- | H |
| 5 | phenyl-$CH_2$- | Cl-phenyl- | H |
| 6 | $CH_3\text{-}(CH_2)_3\text{-}$ | phenyl | H |
| 7 | cyclohexyl | pyridyl (N-containing) | H |
| 8 | cyclohexyl | N-pyridyl (phenyl substituted) | H |
| 9 | phenyl-$CH_2$- | $CH_3O$-phenyl- | H |

TABLE 2

| Melting point | 75–76° C. | | | |
|---|---|---|---|---|
| IR | 1673 cm$^{-1}$ | (C=O) | | |
|  | 1647 cm$^{-1}$ | (C=N) | | |
| NMR | 7.4 ppm | (b, s) | 5H | Ar, H |
|  | 6.4 ppm | (b, s) | 1H | Ph—C—$\underset{\sim}{H}$ |
|  | 6.0 ppm | (b, s) | 1H | $\left.\begin{array}{c}\\ \\\end{array}\right)$ $\underset{\sim}{CH_2}=$ |
|  | 5.5 ppm | (b, s) | 1H | |

TABLE 2-continued

| Melting point | 75–76° C. | | | |
|---|---|---|---|---|
| | 4.5 ppm | (b) | 1H | cyclohexyl H |
| | 2.0 ppm | (s) | 3H | CH₃ |
| | 1.8–0.8 ppm | (b, m) | 10H | cyclohexyl H |

TABLE 3

| Melting point | | | | |
|---|---|---|---|---|
| IR | 1673 cm⁻¹ | (C=O) | | |
| | 1640 cm⁻¹ | (C=N) | | |
| NMR | 7.4 ppm | (d) | 2H | Ar, H |
| | 6.9 ppm | (d) | 2H | Ar, H |
| | 6.4 ppm | (b, s) | 1H | Ph—C—H |
| | 6.0 ppm | (b, s) | 1H | CH₂= |
| | 5.6 ppm | (b, s) | 1H | CH₂= |
| | 4.5 ppm | (b, s) | 1H | cyclohexyl H |
| | 3.75 ppm | (s) | 3H | CH₃O |
| | 1.95 ppm | (s) | 3H | =CH₃ |
| | 1.8–0.8 ppm | (b, m) | 10H | cyclohexyl H |

TABLE 4

| Example | Methacryloyl isocyanate g (mmol) | Azomethine compound g (mmol) | Solvent | Temperature (°C.) | Time (min) |
|---|---|---|---|---|---|
| 3 | 1.0 (9.0) | 1.0 (5.1) | benzene | 20 | 200 |
| 4 | 1.0 (9.0) | 1.0 (4.8) | benzene | 20 | 75 |
| 5 | 1.0 (9.0) | 1.0 (4.3) | benzene | 20 | 40 |
| 6 | 1.0 (9.0) | 1.0 (6.2) | benzene | 20 | 180 |
| 7 | 1.1 (10.0) | 1.7 (9.0) | diethyl ether | 20 | 60 |
| 8 | 1.1 (10.0) | 1.7 (9.0) | diethyl ether | 20 | 60 |
| 9 | 1.0 (9.0) | 1.0 (4.4) | benzene | 20 | 180 |

TABLE 5

Heterocyclic compound

| Example | R⁵ | R⁶ | R⁷ | R⁸ |
|---|---|---|---|---|
| 3 | CH₃ | C₆H₅—CH₂— | C₆H₅— | H |
| 4 | CH₃ | C₆H₅—CH₂— | CH₃—C₆H₄— | H |
| 5 | CH₃ | C₆H₅—CH₂— | Cl—C₆H₄— | H |
| 6 | CH₃ | CH₃(CH₂)₃ | C₆H₅— | H |
| 7 | CH₃ | cyclohexyl— | pyridyl— | H |
| 8 | CH₃ | cyclohexyl— | pyridyl— | H |
| 9 | CH₃ | C₆H₅—CH₂— | CH₃O—C₆H₄— | H |

TABLE 6

| Example | Yield (%) | Melting point (°C.) | IR (cm⁻¹) |
|---|---|---|---|
| 3 | 72 | 74–75 | 1669 (C=O) |
| | | | 1634 (C=N) |
| 4 | 78 | 65–66 | 1671 (C=O) |
| | | | 1636 (C=N) |
| 5 | 97 | 67–68 | 1673 (C=O) |
| | | | 1634 (C=N) |
| 6 | 44 | 68–69 | 1667 (C=O) |
| | | | 1640 (C=N) |
| 7 | 99 | 69–71 | 1671 (C=O) |
| | | | 1634 (C=N) |
| 8 | 89 | 34–35 | 1671 (C=O) |
| | | | 1636 (C=N) |
| 9 | 68 | 132–134 | 1673 (C=O) |
| | | | 1640 (C=N) |

EXAMPLES 9 TO 11

Deuterated chloroform was introduced into a sample tube for measurement of NMR spectrum. Thereto was added the heterocyclic compound represented by the following structural formula (9). Measurement of NMR spectrum was then carried out under the conditions shown in Table 7 to determine the degree of regeneration of methacryloyl isocyanate. The results obtained are shown in Table 7.

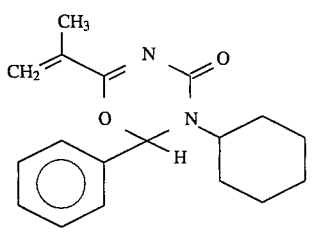
(9)

TABLE 7

| Example | Solvent | Conditions Temperature (°C.) | Time | Degree of regeneration (%) |
|---------|---------|------------------------------|------|----------------------------|
| 9 | deuterated chloroform | 28 | instant | 33 |
| 10 | deuterated chloroform | 48 | instant | 50 |
| 11 | deuterated chloroform | 60 | instant | 75 |

EXAMPLES 12 TO 14

The degree of regeneration of methacryloyl isocyanate was determined in the same manner as in Examples 9 to 11, except that the heterocyclic compound was changed to that represented by the following structural formula (10). The results obtained are shown in Table 8.

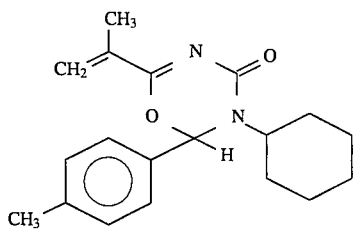
(10)

TABLE 8

| Example | Solvent | Conditions Temperature (°C.) | Time | Degree of regeneration (%) |
|---------|---------|------------------------------|------|----------------------------|
| 12 | deuterated chloroform | 28 | instant | 33 |
| 13 | deuterated chloroform | 45 | instant | 50 |
| 14 | deuterated chloroform | 60 | instant | 75 |

EXAMPLES 15 TO 17

The degree of regeneration of methacryloyl isocyanate was determined in the same manner as in Examples 9 to 11, except that the heterocyclic compound was changed to that represented by the following structural formula (11). The results obtained are shown in Table 9.

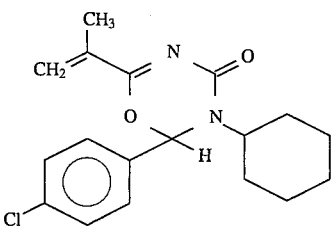
(11)

TABLE 9

| Example | Solvent | Conditions Temperature (°C.) | Time | Degree of regeneration (%) |
|---------|---------|------------------------------|------|----------------------------|
| 15 | deuterated chloroform | 28 | instant | 44 |
| 16 | deuterated chloroform | 45 | instant | 62 |
| 17 | deuterated chloroform | 60 | instant | 75 |

EXAMPLES 18 TO 20

The degree of regeneration of methacryloyl isocyanate was determined in the same manner as in Examples 9 to 11, except that the heterocyclic compound was changed to that represented by the following structural formula (12). The results obtained are shown in Table 10.

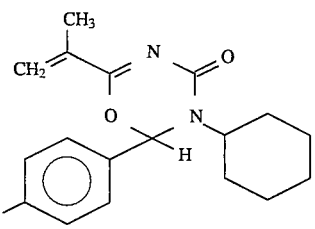
(12)

TABLE 10

| Example | Solvent | Conditions Temperature (°C.) | Time | Degree of regeneration (%) |
|---------|---------|------------------------------|------|----------------------------|
| 18 | deuterated chloroform | 28 | instant | 44 |
| 19 | deuterated chloroform | 45 | instant | 56 |
| 20 | deuterated chloroform | 60 | instant | 76 |

According to the handling method of the present invention, a (2-alkyl)acryloyl isocyanate which is difficult to handle can be easily handled, because the (2-alkyl)acryloyl isocyanate is first converted into a stable heterocyclic compound and the heterocyclic compound is then treated to regenerate the (2-alkyl)acryloyl isocyanate therefrom.

According to the stabilization method of the present invention, a (2-alkyl)acryloyl isocyanate can be extremely easily stabilized by merely adding a given azomethine compound thereto.

According to the method of the present invention for producing a (2-alkyl)acryloyl isocyanate, the (2-alkyl)acryloyl isocyanate can be obtained extremely easily by merely dissolving the stable heterocyclic compound into a solvent.

According to the present invention, a novel heterocyclic compound which is useful in the fields of synthesis chemistry and polymer chemistry can be provided.

According to the method of the present invention for producing a novel heterocyclic compound, the heterocyclic compound which is useful in the fields of synthesis chemistry and polymer chemistry can be produced.

While the invention has been described in detail and with reference to specific embodiments thereof, it will be apparent to one skilled in the art that various changes and modifications can be made therein without departing from the spirit and scope thereof.

What is claimed is:

1. A method for handling a (2-alkyl)acryloyl isocyanate represented by formula (1)

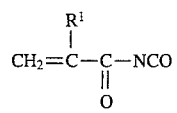
(1)

which comprises the steps of:

reacting an azomethine compound represented by formula (2)

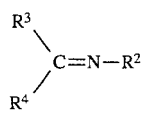
(2)

with the (2-alkyl)acryloyl isocyanate to obtain a reaction product and dissolving the reaction product into a solvent to regenerate the (2-alkyl)acryloyl isocyanate;

wherein $R^1$ represents a hydrogen atom or a lower alkyl group, wherein $R^2$ represents an alkyl group, a cycloalkyl group, an aralkyl group, an alkenyl group, or an alkynyl group, and $R^3$ and $R^4$ each represents a hydrogen atom or a group which does not cause tautomerism with C=N in the formula, provided that at least one of $R^3$ and $R^4$ is not a hydrogen atom.

2. A method for handling a (2-alkyl)acryloyl isocyanate represented by formula (1)

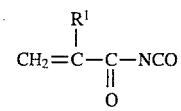
(3)

as claimed in claim 1, wherein said method comprises the steps of:

reacting an azomethine compound represented by formula (2)

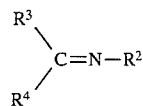
(2)

with the (2-alkyl)acryloyl isocyanate to obtain a heterocyclic compound represented by formula (3)

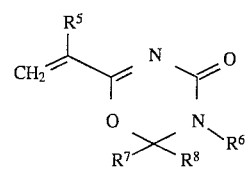
(3)

and dissolving the heterocyclic compound into a solvent to regenerate the (2-alkyl)acryloyl isocyanate;

wherein $R^1$ represents hydrogen or a lower alkyl group, wherein $R^2$ represents an alkyl group, a cycloalkyl group, an aralkyl group, an alkenyl group, or an alkynyl group, and $R^3$ and $R^4$ each represents a hydrogen atom or a group which does not cause tautomerism with C=N in the formula, provided that at least one of $R^3$ and $R^4$ is not a hydrogen atom, wherein $R^5$, $R^6$, $R^7$, and $R^8$ each is the same as $R^1$, $R^2$, $R^3$, and $R^4$, respectively, defined in the formulae (1) and (2).

3. The method as claimed in claim 2, wherein the solvent into which the heterocyclic compound is dissolved is a nonpolar solvent having a dielectric constant of less than 5.

4. The method as claimed in claim 1, wherein an amount of the azomethine compound reacted is from 0.5 to 5 equivalents to the (2-alkyl)acryloyl isocyanate.

5. The method as claimed in claim 1, wherein the reaction between the (2-alkyl)acryloyl isocyanate and the azomethine compound is conducted at a temperature of from −20° to 50° C.

6. The method as claimed in claim 1, wherein the reaction between the (2-alkyl)acryloyl isocyanate and the azomethine compound is conducted in a nonpolar solvent having a dielectric constant of less than 5.

7. A method for stabilizing a (2-alkyl)acryloyl isocyanate represented by formula (1)

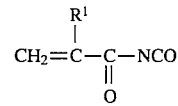
(1)

which comprises the steps of:

preparing an azomethine compound represented by formula (2)

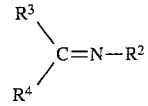
(2)

and reacting the azomethine compound with the (2-alkyl)acryloyl isocyanate to form a heterocyclic compound represented by formula (3)

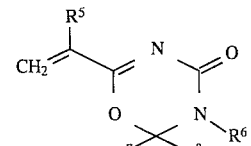
(3)

wherein $R^1$ represents a hydrogen atom or a lower alkyl group, wherein $R^2$ represents an alkyl group, a cycloalkyl group, an aralkyl group, an alkenyl group, or an alkynyl group, and $R^3$ and $R^4$ each represents a hydrogen atom or a group which does not cause tautomerism with C=N in the formula, provided that at least one of $R^3$ and $R^4$ is not a hydrogen atom, wherein $R^5$, $R^6$, $R^7$, and $R^8$ each is the same as $R^1$, $R^2$, $R^3$, and $R^4$, respectively defined in the formulae (1) and (2) given above.

8. A heterocyclic compound represented by formula (3):

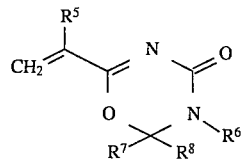
(3)

wherein $R^5$ represents a hydrogen atom or a lower alkyl group, $R^6$ represents an alkyl group, a cycloalkyl group, an aralkyl group, an alkenyl group, or an alkynyl group, and $R^7$ and $R^8$ each represents a hydrogen atom or a group in which a carbon atom located in the α-position to carbon atoms constituting a heterocyclic ring does not have a hydrogen atom, provided that at least one of $R^7$ and $R^8$ is not a hydrogen atom.

9. A method for producing a heterocyclic compound represented by formula (3)

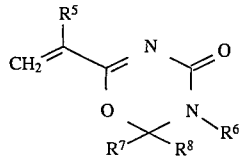
(3)

which comprises the steps of:

preparing a (2-alkyl)acryloyl isocyanate represented by formula (1)

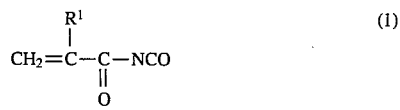
(1)

preparing an azomethine compound represented by formula (2)

(2)

and reacting the (2-alkyl)acryloyl isocyanate with the azomethine compound;

wherein $R^1$ represents a hydrogen atom or a lower alkyl group, wherein $R^2$ represents an alkyl group, a cycloalkyl group, an aralkyl group, an alkenyl group, or an alkynyl group, and $R^3$ and $R^4$ each represents a hydrogen atom or a group which does not cause tautomerism with C=N in the formula, provided that at least one of $R^3$ and $R^4$ is not a hydrogen atom, wherein $R^5$ represents a hydrogen atom or a lower alkyl group, $R^6$ represents an alkyl group, a cycloalkyl group, an aralkyl group, an alkenyl group, or an alkynyl group, and $R^7$ and $R^8$ each represents a hydrogen atom or a group in which a carbon atom located in the α-position to carbon atoms constituting a heterocyclic ring does not have a hydrogen atom, provided that at least one of $R^7$ and $R^8$ is not a hydrogen atom.

10. The method as claimed in claim 2, wherein the solvent into which the heterocyclic compound is dissolved is a polar solvent having a dielectric constant of 5 or more.

* * * * *